United States Patent [19]

Haack et al.

[11] Patent Number: 5,026,491

[45] Date of Patent: Jun. 25, 1991

[54] CONTROLLING SULFATE REDUCING BACTERIA BY SLUG DOSING WITH QUICK-KILL ANTIMICROBIALS AND BY CONTINUOUS DOSING WITH ISOTHIAZOLONES

[75] Inventors: Thomas K. Haack, North Wales; David E. Greenley, Blue Bell, both of Pa.

[73] Assignee: Rohm and Haas Company, Philadelphia, Pa.

[21] Appl. No.: 503,203

[22] Filed: Mar. 30, 1990

Related U.S. Application Data

[63] Continuation-in-part of Ser. No. 179,698, Apr. 11, 1988, abandoned.

[51] Int. Cl.$^5$ .............................................. E21B 41/02
[52] U.S. Cl. .............................. 252/8.552; 252/8.554; 166/312; 166/902
[58] Field of Search .......................... 252/8.552, 8.554; 166/312, 902

[56] References Cited

PUBLICATIONS

J. L. Lynch and R. G. J. Edyvean, "Biofouling in Oilfield Water Systems-A Review", Biofouling 1988, vol. 1, pp. 147–162.
R. Cord-Ruwisch, W. Kleintz, F. Widdel, "Sulfate-Reducing Bacteria and the Activities in Oil Production," Society of Petroleum Engineers 1987, SPE 13554.

*Primary Examiner*—Robert L. Stoll
*Assistant Examiner*—Gary L. Geist
*Attorney, Agent, or Firm*—Michael B. Fein

[57] ABSTRACT

A method is described whereby quick-kill and maintenance antimicrobials are used to control biofouling of oil production water injection systems.

10 Claims, No Drawings

CONTROLLING SULFATE REDUCING BACTERIA BY SLUG DOSING WITH QUICK-KILL ANTIMICROBIALS AND BY CONTINUOUS DOSING WITH ISOTHIAZOLONES

This application is a continuation-in-part of Ser. No. 179,698 filed Apr. 11, 1988, now abandoned.

BACKGROUND OF THE INVENTION

The injection of water into subterranean oil bearing formations is a common practice for increasing the amount of oil that can be recovered. As the water flows through the formation rock it pushes oil towards the producing wells. The most common material for constructing the above ground portion of water injection systems is mild steel. To minimize corrosion of the steel, oxygen present in the injection water must be removed. However, once the oxygen is removed, an ideal environment is created for the growth of sulfate reducing bacteria.

Sulfate reducing bacteria can grow in the water as planktonic organisms, or attached to the pipe walls as sessile organisms. Bacteria which grow attached to surfaces are commonly referred to as "biofilm." Sulfate reducing bacteria growing as biofilms in water injection systems can cause several serious problems. The most serious of these problems is that of microbial induced corrosion. It is well known that sulfate reducing bacteria can cause significant damage to water injection systems by corroding deep pits and holes that can completely penetrate the pipe walls. Antimicrobial chemicals are commonly added to the water in order to control the growth of sulfate reducing bacteria. The problems caused by sulfate reducing bacteria are discussed in *Biofouling in Oilfield Water Systems—A Review*, J. L. Lynch and R. G. J. Edyvean, BIOFOULING 1988, Vol 1, pp. 147–162 and in *Sulfate-Reducing Bacteria and the Activities in Oil Production*, R. CordRuwisch, W. Kleintz, F. Widdel, Society of Petroleum Engineers 1987, SPE 13554.

DESCRIPTION OF THE PRIOR ART

Antimicrobial compounds are commonly added to the injection water to control the growth of sulfate reducing bacteria (hereinafter referred to as SRB). Many different antimicrobial compounds have been used to control biofilm growth; these include formaldehyde and alkanedials such as glutaraldehyde, cationic polymeric biguanides, quaternary ammonium compounds, quaternary phosphonium compounds, phenolics and thiocyanates. These antimicrobials were selected based on their ability to quickly kill SRB. These particular antimicrobials, hereinafter referred to as "quick-kill antimicrobials," are characterized by high "speed-of-kill" (SOK) or "knock-down" properties, usually requiring relatively high dosage concentrations, e.g., greater than about 20 ppm, based on weight of injection water, and usually greater than about 50 ppm, to be effective. Glutaraldehyde (1,5-pentanedial) is by far the most commonly used oilfield quick-kill antimicrobial. It is often combined with other quick-kill antimicrobials such as quaternary ammonium compounds so as to increase the speed with which it kills bacteria. Quick-kill antimicrobials are added to the water injection system as slug doses. By "slug dose" we mean addition in one portion or shot over a relatively short period of time by metered delivery, rather than over an extended period of time. Typically, the quick-kill antimicrobial is added once every 7 days for 2–6 hours at a time.

Slug dosing of antimicrobials results in a "saw tooth" pattern when considering the sessile population of SRB present in the system. High population levels of biofilm bacteria are quickly reduced by application of the quick-kill antimicrobial. As soon as the quick-kill antimicrobial addition is completed, however, the bacteria in the biofilm commence a period of rapid regrowth. The biofilm bacteria can quickly repopulate to levels equal to those present before the quick-kill antimicrobial slug dose was added. It is during the period of rapid regrowth that the bacteria are most active and can cause the most damage.

SUMMARY OF THE INVENTION

It is an object of the invention to provide an improved process for controlling biological contamination and their corrosive processes, in oilfield water systems. It is also an object to provide a process which enables lower levels of antimicrobials to be used at less frequent intervals compared to those required by prior art processes.

These objects, and other which will become apparent from the following disclosure, are achieved by the present invention which comprises in one aspect the substantially continuous addition of a maintenance antimicrobial in combination with a slug dose of quick-kill antimicrobial in a water injection system for oil recovery.

In another aspect, the invention comprises an improved process for controlling biological contamination and microbial-induced corrosion of oil production water systems by sessile bacteria wherein intermittent slug doses of a quick-kill antimicrobial are applied to said water, the improvement comprising substantially continuously dosing of said water with a maintenance antimicrobial.

DETAILED DESCRIPTION OF THE INVENTION AND THE PREFERRED EMBODIMENTS

Surprisingly, it has been discovered that the rapid regrowth of biofilm SRB following a slug dose application of quick-kill antimicrobial can be reduced significantly by the substantially continuous addition of a "maintenance" antimicrobial after the initial slug dose of quick-kill antimicrobial. By "maintenance" antimicrobial we mean antimicrobials which are particularly effective at relatively low dosage concentrations, e.g., less than about 5 ppm active ingredient based on weight of injection water, and usually less than about 3 ppm, and may or may not also possess high SOK properties.

Typically, quick-kill antimicrobials alkanedials, such as glutaraldehyde and formaldehyde, cationic polymeric biguanides, quaternary ammonium compounds, cocodiamine, acrolein, 2-bromo-2-nitropropanediol, dibromonitrilopropionamide, ADBACs or alkyldimethylbenzylammoniumchlorides, quaternary phosphonium compounds, phenolics and thiocyanates. Other examples of alkanedials which can be used include propanedial, butanedial, and hexanedial. Levels of alkanedial to be used will vary depending upon the degree of biofouling in the system. Typically, slug doses ranging from 20 to 4000 ppm, preferably 50–1000 ppm, can be used. The alkanedial may be used in combination with other antimicrobial such as quaternary ammonium compounds, (as is well known in the art) to accomplish the best initial reduction in the biofilm population.

Additions of the alkanedial quick-kill "knock-down" antimicrobial may need to be repeated at some interval, for example once every seven to thirty days, to maintain optimal control of the system.

Combinations of compatible quick-kill antimicrobials can be used. For example, quaternary ammonium compounds can be used with alkanedials. The preferred level of quaternary is from about 10 to about 50% by weight of the alkanedials.

Addition of maintenance antimicrobials may be done on a scheduled basis where small shots are added, or the antimicrobial may be added through a metering pump. It is preferred to add the maintenance antimicrobial in aqueous or aqueous-compatible systems, such as water solution or emulsified dispersion.

Suitable maintenance antimicrobials include MBT (methylene-bis-thiocyanate), DBNPA (dibromonitrilo-propionamide), metronidazole (2-methyl-5-nitroimidazole-1-ethanol), acrolein, cocodiamine and isothiazolones. Isothiazolones of the formula (I):

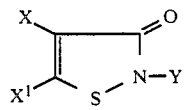

(I)

wherein Y is $(C_1-C_8)$alkyl or $(C_3-C_8)$cycloalkyl, X is H or Cl, and $X^1$ is H or Cl, are preferred, especially the mixture of 5-chloro-2-methyl-3-isothiazolone and 2-methyl-3-isothiazolone which is particularly efficient and cost effective. The preferred levels of maintenance antimicrobials are from about 0.25 ppm to about 2.5 ppm based on weight.

Surprisingly the use of the maintenance antimicrobial provides a method wherein the frequency of quick-kill antimicrobial can be reduced.

The combination of quick-kill antimicrobial and isothiazolone is effective in salt or fresh water at any temperature that will support microbial growth. The systems may be static, but in operation, there is motion of water throughout the system. The combination is functional in systems exposed to oxygen, but will generally be used where the oxygen content is reduced for reasons such as corrosion resistance.

Another advantage of the use of the maintenance and quick-kill antimicrobials is that any tolerance by the SRB to one antimicrobial, leading to increased populations even in the presence of that antimicrobial, may be counteracted by use of the other antimicrobial.

EXPERIMENTAL

A biofouling loop was designed to simulate the activity of sessile SRB.

The test loop components are made up of an oxygen scrubbing system, a seawater salt-nutrient concentrate, a continuous inoculum source for SRB, a mixing chamber, an entry water reservoir, a recirculation system and a mild steel sampling section.

1. Removal of oxygen from the fluid entering a mild steel device for studying biofilm is required for the rapid establishment of a stable SRB biofilm.

Deionized water from a constant supply flows through three serial nitrogen sparge cylinders. Ammonium bisulfite is metered into the third sparge cylinder. Dissolved oxygen in the deionized water is reduced from 7-9 ppm to <50 ppb by this treatment.

2. A seawater salt-nutrient concentrate solution is pumped into the mixing chamber (below) at a rate of 25% of the total fluid flow. The seawater concentrate is also sparged with nitrogen.

3. The source of SRB biofilm inoculum is a fixed film reactor (FFR). The FFR is a one liter graduated cylinder packed with sterile granitic rock that was inoculated with a mixed culture of aerobic bacteria and SRB from North Sea injection water. A seawater nutrient solution containing 60 mg TSB (trypticase soy broth) per liter is pumped through the rockpile at a rate of six liter per day. The effluent from the rockpile is the source of a mixed population of bacteria which can rapidly foul the circulating test loops.

4. The mixer is the source of entry water for each of eight recirculating test loops operating in parallel. Use of a mixer insures that each circulating test loop receives an identical entry water feed and greatly reduces the number of pumps and water-carrying lines required for the operation of multiple test loops.

5. The entry water reservoir is constructed of PVC pipe and fittings. This is the point of water addition to and drainage from each circulating test loop, and is an integral part of the loop. Fluid is pumped into each circulating loop at a rate of 10 ml per minute. An overflow line maintains a constant volume in the recirculating test loops. Each circulating test loop normally contains 300 ml of anaerobic seawater and the fluid retention time is 30 minutes.

6. Circulation in this system is provided by a magnetic drive centrifugal pump. Flow in the mild steel sampling section is normally 0.6 meters per second. Flow rates can be monitored by either a paddlewheel or magnetic flow sensor, and are controlled with a regulating valve. Neoprene tubing is used to connect the components of the circulating test loop to minimize oxygen diffusion into the loops.

7. The mild steel tube sampling section is an 80 cm length of 1.27 cm o.d. seamless mechanical tubing with an 0.08 cm wall.

To sample the biofilm the outer wall of the mild steel tube is wiped with ethanol and a two cm piece cut off with a tubing cutter. This yields a coupon with a 7.0 $cm^2$ sample surface. The inside of the coupon is rinsed with sterile artificial sea water. The biofilm is scraped from the coupon with a sterile microspatula. The biofilm and the coupon are placed in a stoppered tube containing 10 ml of sterile anaerobic artificial seawater and sonicated for one minute in an ultrasonic cleaning bath to disperse the biofilm. Viable counts of SRB and aerobic bacteria are determined by the most probable number (MPN) technique.

Viable aerobic bacteria counts are determined with a medium containing 20 gm TSB per liter. The SRB growth medium is a modification of that used in API RP 38 (Standard test method published by American Petroleum Institute). N-Tris[hydroxymethyl]methyl-2-amino-ethanesulfonic acid is used to buffer the medium in place of phosphate. The medium is supplemented with ammonium, calcium and trace metals. The SRB medium is dispensed anaerobically in disposable Hungate-type tubes (Bellco Glass, Inc.). SRB tubes are incubated for one week after inoculation and scored for growth. Experience indicates that SRB counts are maximized within this time period.

pH is determined with a calomel combination microelectrode. Total sulfide is determined using the methylene blue assay. Dissolved oxygen is measured using a CHEMets instrument (CHEMetrics, Inc.).

Glutaraldehyde was added as either a 20% aqueous solution or as a 20% aqueous solution containing 5% of a quaternary ammonium compound. The isothiazolone mixture is a 1.5% aqueous solution of a mixture of the chlorinated and non-chlorinated materials (75% 5-chloro-2-methyl-3-isothiazolone and 25% 2-methyl-3-isothiazolone). Concentrations of glutaraldehyde (designated "Glut" in the Examples), quaternary ammonium compounds (designated "Quat" in the Examples), and isothiazolones (designated "Isot" in the Examples) are expressed as ppm "active ingredient," hereinafter referred to as ppm AI.

EXAMPLE 1

(Comparative)

Quick-Kill Efficacy

The following data show values for SRB populations (log format) as a function of the quick-kill (knockdown) treatment. The water system was allowed to foul (no treatment) prior to withdrawing samples for treatment and measurement. The samples were slug dosed with different combinations of antimicrobials for 2 or 4 hours, after which viable population counts of SRB were obtained.

| Treatment | | | | Quick-Kill Effect |
|---|---|---|---|---|
| Quat ppm | Glut ppm | Time hrs | Log SRB/cm$^2$ | (Log{control}-Log{treatment}) |
| 0 | 0 | 2-4 | 7.3-7.5 | Control |
| 25 | 100 | 4 | 2.3 | 5.1 |
| 50 | 200 | 2 | 2.0 | 5.4 |
| 0 | 100 | 4 | 0.6 | 6.8 |
| 0 | 200 | 2 | 0.6 | 6.8 |
| 25 | 0 | 4 | 7.0 | 0.4 |
| 100 | 0 | 2 | 6.5 | 0.9 |

As can be seen from the experimental data, the Quat alone treatments had no significant quick-kill effects (change in Log SRB/cm$^2$ less than 2) at concentrations from 25-100 ppm, whereas the Glut or Glut/Quat combinations have very large quick-kill effects (change in Log SRB/cm$^2$ greater than 5) at concentrations of 25-200 ppm.

EXAMPLE 2

(Comparative)

SRB Regrowth after Quick-Kill Without Maintenance Antimicrobial

The following data show the effect of Glut and Glut/Quat combinations used as slug dose treatments on SRB in a biofilm. The system was allowed to foul for four weeks prior to starting treatment and withdrawal of samples for measurement of SRB populations (log format). SRB populations were measured at one week intervals just before and just after the slug dose treatments. After withdrawal of samples, the water system was slug dosed twice/week.

| Treatment | | | Quick-Kill Effect |
|---|---|---|---|
| Quat ppm | Glut ppm | Time wks | Log SRB/cm$^2$ | (Log{before treat}-Log{treatment}) |
| 0 | 0 | 1 | 4.6 | |
| 37 | 150 | 1 | <1.0 | >3.6 |
| 0 | 0 | 2 | 4.7 | |
| 37 | 150 | 2 | <1.0 | >3.7 |
| 0 | 0 | 3 | 3.6 | |
| 37 | 150 | 3 | <1.0 | >2.6 |
| 0 | 0 | 4 | 3.3 | |
| 37 | 150 | 4 | 3.5 | -0.2 |
| 0 | 0 | 5 | 5.1 | |
| 37 | 150 | 5 | 4.5 | 0.6 |

Although the slug dose technique rapidly reduced the SRB population in the early portion of the experiment, within one week the initial population reestablished itself. Thus, although Glut/Quat was an effective quick-kill combination in weeks #1 through #3, SRB populations always exceeded 1000 (log SRB/cm$^2$>3) within one week, indicating rapid regrowth. Further, the relatively ineffective quick-kill properties (change in log SRB/cm$^2$<1) observed in the later weeks (#4 and #5) may indicate development of tolerance by the SRB for the Glut/Quat quick-kill antimicrobial combination.

EXAMPLE 3

(Invention)

SRB Control With Quick-Kill and Maintenance Antimicrobials

The procedure of Example 2 was repeated except that Isot was metered in at 0.5 ppm continuously after the initial slug dose of Glut/Quat at week #1. The data show that SRB in the water injection system were successfully controlled using only the initial slug dose of quick-kill Glut/Quat antimicrobial, and the continuous Isot treatment, i.e., no additional slug doses were required. Specifically, SRB were controlled below a level of undesirable buildup (about 1000 SRB/cm$^2$, i.e., log SRB/cm$^2$<3) for at least 4 weeks due to the use of continuous dosing with 0.5 ppm Isot maintenance antimicrobial.

In contrast, the absence of continuous dosing with a maintenance antimicrobial (Example 2) resulted in log SRB/cm$^2$ values <3 within one week of quick-kill slug dose treatment. Note that the "treatment effect" (change in log SRB/cm$^2$>4) with 0.5 ppm continuous Isot is comparable to the quick-kill effect of Glut/Quat, but has been achieved for a longer period of time without need for frequent slug doses of Glut/Quat.

| Treatment | | | | | Treatment Effect |
|---|---|---|---|---|---|
| Isot ppm | Quat ppm | Glut ppm | Time wks | Log SRB/cm$^2$ | (Log{before treat}-Log{treatment}) |
| 0 | 0 | 0 | 0 | 6.5 | — |
| 0 | 0 | 0 | 1 | 6.5 | — |
| 0 | 37 | 150 | 1 | <1.0 | >5.5 |
| 0.5* | 0 | 0 | 1 | — | — |
| 0.5 | 0 | 0 | 2 | 1.3 | 5.2 |
| 0.5 | 0 | 0 | 3 | 1.2 | 5.3 |
| 0.5 | 0 | 0 | 4 | 2.2 | 4.3 |
| 0.5 | 0 | 0 | 5 | 2.2 | 4.3 |

*start of continuous 0.5 ppm Isot dose

EXAMPLE 4

(Comparative)

The Use of Maintenance Antimicrobial Without Use of Quick-Kill Antimicrobial

The conditions of Example 3 were repeated except that no quick-kill antimicrobial was used. In this case the Isot was continuously added at 0.5 ppm with the following results.

| Treatment | Days of Operation | Log SRB/cm$^2$ |
| --- | --- | --- |
| None (control) | 4 | 5.3 |
| | 7 | 8.3 |
| | 11 | 8.3 |
| | 17 | 8.0 |
| Isot (0.5 ppm) | 4 | 3.5 |
| | 7 | 4.5 |
| | 11 | 3.5 |
| | 7 | 4.3 |

Although the continuous Isot dosing technique reduces the SRB populations compared to the control, the SRB levels are still undesirably high, i.e., greater than 1000 SRB/cm$^2$ (and greater than 10,000 in some cases, e.g., log SRB/cm$^2$ >4 at 7 and 17 days).

Only when the continuous maintenance and slug dose quick-kill antimicrobials are used together according to the invention (as in Example 3) are the SRB "knocked-down" sufficiently for the continuous maintenance antimicrobial to control SRB below undesirable levels (log SRB/cm$^2$ <3).

We claim:

1. In a process for controlling biological contamination of oil production water injection systems by sulfate-reducing sessile bacteria wherein a slug dose of a quick-kill antimicrobial selected from one or more of the group consisting of (C$_3$–C$_7$)alkanedials, formaldehyde, cationic polymeric biguanides, quaternary ammonium compounds (alkyldimethylbenzylammonium chlorides), quaternary phosphonium compounds, phenolics, cocodiamine, 2-bromo-2-nitropropanediol, acrolein, dibromonitrilopropionamide and organic thiocyanates is applied to said injection water, the improvement comprising substantially continuously dosing said injection water at a concentration of about 0.25 to 5 ppm based on the weight of injection water with a maintenance antimicrobial selected from the group consisting of an isothiazolone of the formula

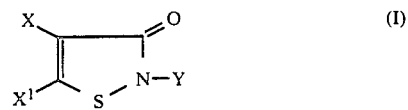

wherein Y is (C$_1$–C$_8$)alkyl or (C$_3$–C$_8$)cycloalkyl, X is H or Cl, and X$^1$ is H or Cl.

2. The process of claim 1 wherein the quick-kill antimicrobial is a mixture of glutaraldehyde and a quaternary ammonium compound.

3. The process according to claim 1 wherein the maintenance antimicrobial comprises 5-chloro-2-methyl-3-isothiazolone.

4. The process according to claim 1 wherein the quick-kill antimicrobial comprises glutaraldehyde and the maintenance antimicrobial comprises 5-chloro-2-methyl-3-isothiazolone.

5. The process according to claim 4 wherein said glutaraldehyde is added in an amount from about 50 to 4000 ppm and said 5-chloro-2-methyl-3-isothiazolone is added admixture with 2-methyl-3-isothiazolone in an amount from about 0.25 ppm to 5 ppm active ingredient based on weight of injection water.

6. The process according to claim 4 wherein said glutaraldehyde is added in an amount from about 50 to 4000 ppm every 5 to 15 days and said 5-chloro-2-methyl-3-isothiazolone is added in an amount from about 0.25 ppm to 5 ppm.

7. The process according to claim 4 wherein said glutaraldehyde is added in an amount from about 50 to 4000 ppm every 30 to 60 days and said 5-chloro-2-methyl-3-isothiazolone is added in an amount from about 0.25 ppm to 5 ppm.

8. The process according to claim 1 wherein said quick-kill antimicrobial is added whenever the sulfate reducing sessile bacteria surpass a population count of about 1000 SRB/cm$^2$.

9. The process of claim 1 wherein the sessile bacteria are sulfate-reducing.

10. The process of claim 1 wherein the control of biological contamination is conducted in the substantial absence of oxygen.

* * * * *